(12) United States Patent
Kim

(10) Patent No.: US 6,447,291 B2
(45) Date of Patent: Sep. 10, 2002

(54) ORTHODONTIC JIG FOR ATTACHING ORTHODONTIC BRACKETS

(76) Inventor: Joong Han Kim, 301-1310 Banpomido Apt. #80-4, Banpo-dong, Seocho-Gu, Seoul (KR), 137-040

( * ) Notice: Subject to any disclaimer, the term of this patent is extended or adjusted under 35 U.S.C. 154(b) by 0 days.

(21) Appl. No.: 09/749,794

(22) Filed: Dec. 28, 2000

(30) Foreign Application Priority Data

| Dec. 31, 1999 | (KR) | 99-68382 |
|---|---|---|
| Dec. 31, 1999 | (KR) | 99-68386 |
| Dec. 31, 1999 | (KR) | 99-68387 |
| Dec. 19, 2000 | (KR) | 2000-78551 |
| Dec. 19, 2000 | (KR) | 2000-78553 |

(51) Int. Cl.[7] .............................................. A61C 3/00
(52) U.S. Cl. ............................ 433/4; 433/24; 606/211
(58) Field of Search ............................ 433/3, 8, 9, 24, 433/4; 606/210, 211, 205, 206, 208

(56) References Cited

U.S. PATENT DOCUMENTS

| 3,686,762 A | * | 8/1972 | Sutter ............................. 433/3 |
| 4,035,919 A | * | 7/1977 | Cusato ............................ 433/3 |
| 4,134,208 A | | 1/1979 | Pearlman |
| 4,422,849 A | | 12/1983 | Diamond |
| 4,455,137 A | | 6/1984 | Diamond |
| 4,474,555 A | | 10/1984 | Diamond |
| 4,478,576 A | * | 10/1984 | Maijer et al. .................. 433/3 |
| 4,487,580 A | * | 12/1984 | Ridgeway ....................... 433/3 |
| 4,850,864 A | * | 7/1989 | Diamond ........................ 433/3 |
| 5,062,793 A | * | 11/1991 | Cleary et al. .................. 433/3 |
| 5,542,842 A | | 8/1996 | Andreiko et al. |
| 5,868,787 A | | 2/1999 | Kim |
| 6,123,544 A | | 9/2000 | Cleary |
| 6,290,495 B1 | * | 9/2001 | Abri ............................... 433/3 |

\* cited by examiner

*Primary Examiner*—Todd E. Manahan
(74) *Attorney, Agent, or Firm*—Jacobson Holman, PLLC

(57) ABSTRACT

An orthodontic jig for attaching orthodontic brackets on the teeth is disclosed. The orthodontic jig comprises a housing, a bracket support extending out of the front side of the housing through the back side of the housing, tweezers for gripping the tie wings of the bracket connected to the housing and disposed around the bracket support, a cusp tip reference means for setting the cusp tip of the tooth as the reference surface of the orthodontic position, means for displacing the cusp tip reference plate upward or downward, and a handle connected to the upper and lower surface of housing for supporting the housing.

The orthodontic jig can be connected with a cusp tip reference means or/and a lingual bracket positioning device.

20 Claims, 20 Drawing Sheets

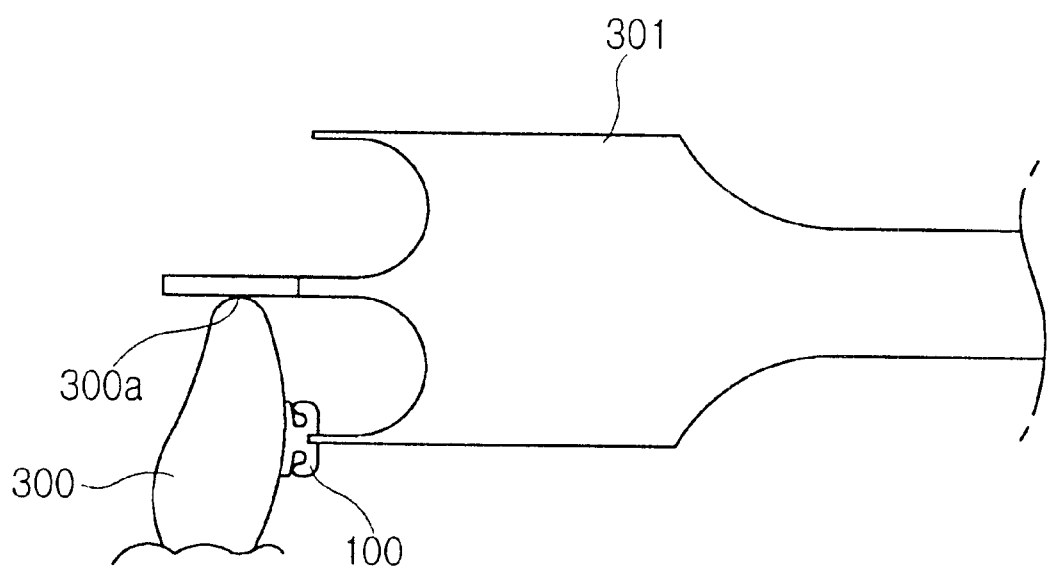

ORTHODONTIC JIG FOR ATTACHING ORTHODONTIC BRACKETS

BACKGROUND OF THE INVENTION

The present invention relates to an orthodontic jig used for affixing brackets to a patient's tooth, and more particularly to orthodontic jig for positioning and affixing the brackets to an anterior tooth and a posterior tooth.

Generally, as can be seen in FIG. 2a and FIG. 2b, an orthodontic bracket 100 is comprised of a base 101, a slot 102a, an identification mark 104, and tie wings 102.

The base 101 is slightly larger than the center section of the bracket 100 and is concave to conform to the surface of the patient's tooth. The chambered slot 102a is slightly angled to the horizontal center line of the bracket 100 to receive an arch wire 103 which makes an ideal dentition. The tie wing 102, being of rhomboidal construction, is used for securing the labial tooth surface's not coming in contact with a ligature wire 105. The identification mark allows an orthodontist quicker identification when rebonding a loose bracket. The ligature wire 105 holds the arch wire 103 which will make the ideal dentition after the bracket 100 is glued to the patient's tooth. The stem is integrally formed on the base 101 in order to receive the ligature wire 105 or an elastic ligature.

To make a functional dentition, the orthodontist must glue the bracket 103 accurately 3.5 mm~5 mm away from the end of the tooth and rapidly onto the surface of the tooth, because orthodontic bonding materials are congealed within 30 seconds. Simultaneously, the orthodontist must glue the bracket 100 parallel to the vertical axis of the tooth, referring to a vertical scribe line (not shown) of the bracket 100.

Conventional orthodontic tweezers are, for example, a cross-over type as can be seen in FIG. 2b, the cross-over type has a gripping jaw which is held in the closed position by tension formed by the shape of the tweezers. The user must apply pressure to the members to open the jaw align the object upon which the tweezers are to be used with, and then reduce the pressure on the members so that the object is held by the gripping area.

The cross-over type is referred over other designs for work requiring the object to be held securely and accurately, as the amount of pressure applied by the user. This is especially crucial in the orthodontics field and in the placement of brackets on the patient's teeth, because such brackets are very small and must be held securely and located precisely. Therefore, the preferred embodiment of the tweezers, and could also embody tweezers which are not the cross-over type.

On the other hand, to attach the bracket to the patient's tooth, the orthodontist generally uses various conventional tweezers for gripping the bracket. Also, to measure distance between the end of tooth and the bracket, the orthodontist generally uses a gauge comprising four different measurement tooth or uses the naked eye. Using one or both of these methods, the orthodontist ascertains whether the bracket is in an accurate position.

However, the conventional tweezers have limitations in that the bracket is sometimes not in an accurate and precise position and it takes the orthodontist a lot of time to attach the bracket.

An orthodontic tweezers with a gauge, as shown in FIG. 3a of U.S. Pat. No. 5,868,787, are proposed to overcomes the above mentioned limitations of the conventional tweezers. Tweezers with a gauge in the U.S. Pat. No. 5,868,787 can help the user attach the brackets more accurately and precisely to the patient's tooth and will serve well in the orthodontic field. Also, the user, using the tweezers can attach the brackets more quickly to the patient's tooth with greater comfort.

However, the disadvantage of this tweezers is that it is difficult for the orthodontist to attach the brackets to molars because of the oral structure. Also, due to the height difference between the adjacent teeth, it is difficult to attach the bracket to the accurate orthodontic position. Also, the orthodontist cannot attach the bracket to the lingual surface of the teeth with this tweezers.

SUMMARY OF THE INVENTION

It is an object of this invention to provide an orthodontic jig for attaching and positioning various brackets with ease and with high accuracy although required position may vary on the molar or incisor.

It is another object of this invention to provide an orthodontic jig for attaching and positioning brackets with high accuracy when the size, torque, and angulation of the teeth are not uniform and the height difference between the adjacent teeth is very large.

It is further object of this invention to an orthodontic jig for attaching and positioning various brackets with ease and with high accuracy although required position may vary on the labial or lingual surface of the teeth.

In order to achieve the above object, the present invention provides an orthodontic jig for positioning a orthodontic bracket comprising a housing; a bracket support extending out of the front side of the housing through the back side of the housing; tweezers for gripping the tie wings of the bracket connected to the housing and disposed around the bracket support; a cusp tip reference means for setting the cusp tip of the tooth as the reference surface of the orthodontic position; means for displacing the cusp tip reference plate upward or downward; and a handle connected to the upper and lower surface of housing for supporting the housing.

The present invention still provides an orthodontic jig for positioning a orthodontic bracket comprising tweezers including two cross over extended parts which is provided with a gripping tip to grip the tie wing of the labial bracket; a housing including a tweezers support connected with the edge of the tweezers, and a height gauge disposed between the extended parts and connected with a height adjusting screw; a bracket support inserted through the housing, wherein one edge thereof is formed with 'T' shape and the other edge thereof includes a rotation adjusting handle; and a cusp tip reference plate fixed with the upper edge of the height gauge for setting the orthodontic position of the bracket from the cusp tip gauge.

The present invention further provides an orthodontic jig with the cusp tip reference means comprising a cusp tip reference plate connected to the displacing means; a frame having a connecting rod and a channel connected with the cusp tip reference plate; panels disposed at each side of the frame; an occlusal fossae positioning pin connected with the panel for coming in contact with the occlusal fossae of a molar; and span adjusting means connected to the panels for adjusting the span between the panels.

The present invention further provides an orthodontic jig with the lingual bracket positioning device comprising a vertical frame; a lingual bracket support plate inserted into the slot of the lingual bracket; a lingual bracket tweezers connected to the vertical frame for gripping the tie wings of the lingual bracket; a vertical panel including a hole connected to the cusp tip reference means, a scale disc provided with an elongated hole on a concentric circle and a connecting hole connected to the lingual bracket support plate at the center of the disc; and a lingual bracket tweezers connected to the cusp tip reference means for gripping the tie wings of the lingual bracket.

BRIEF DESCRIPTION OF THE DRAWINGS

The above and other features, objects and advantages of the present invention will be better understood from the following detailed description of the invention when read in conjunction with the accompanying drawings in which.

DETAILED DESCRIPTION OF THE INVENTION

Figure 4A:
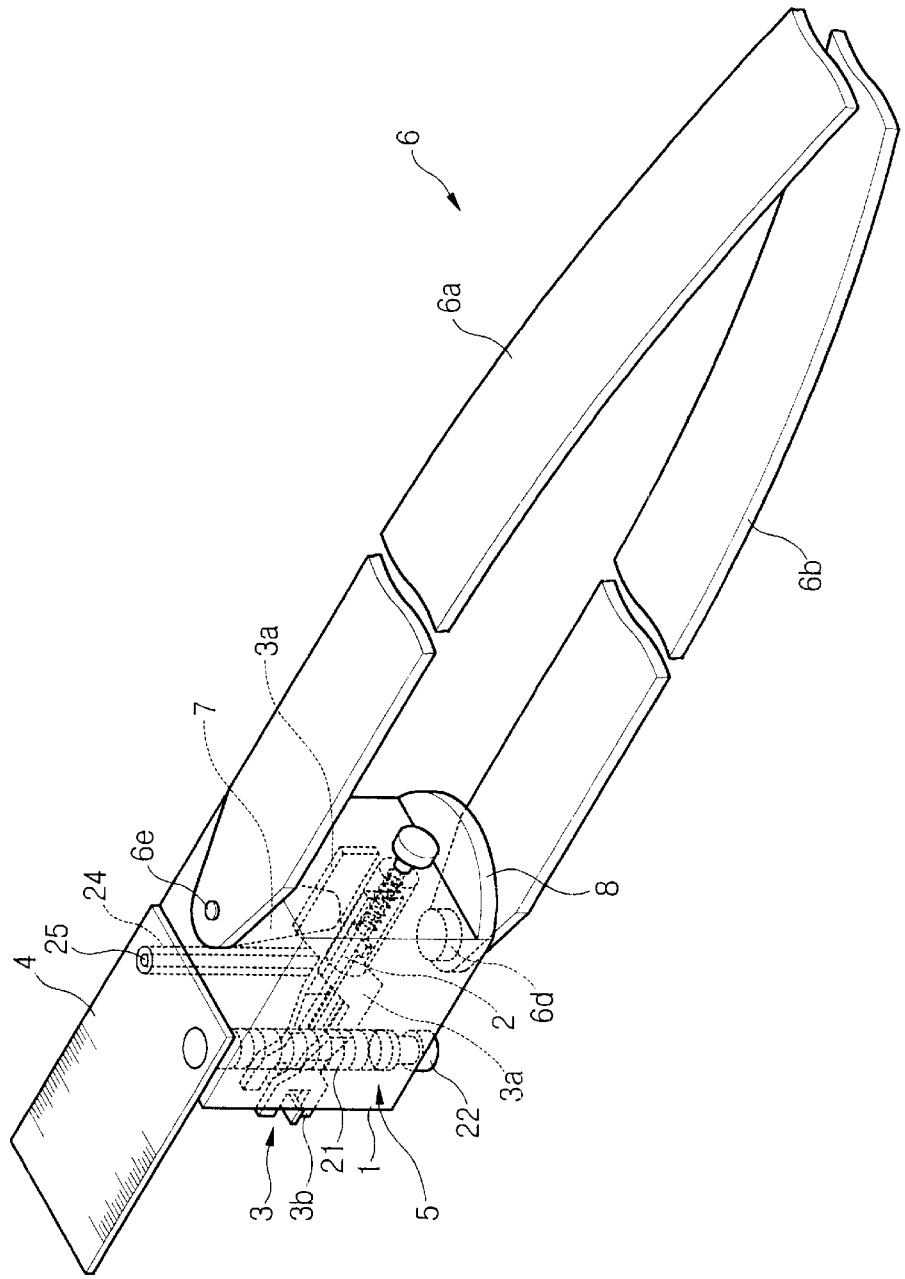
FIG. 4a is a perspective view of an orthodontic jig for attaching and position brackets according to an embodiment of the present invention.
Figure 4B:
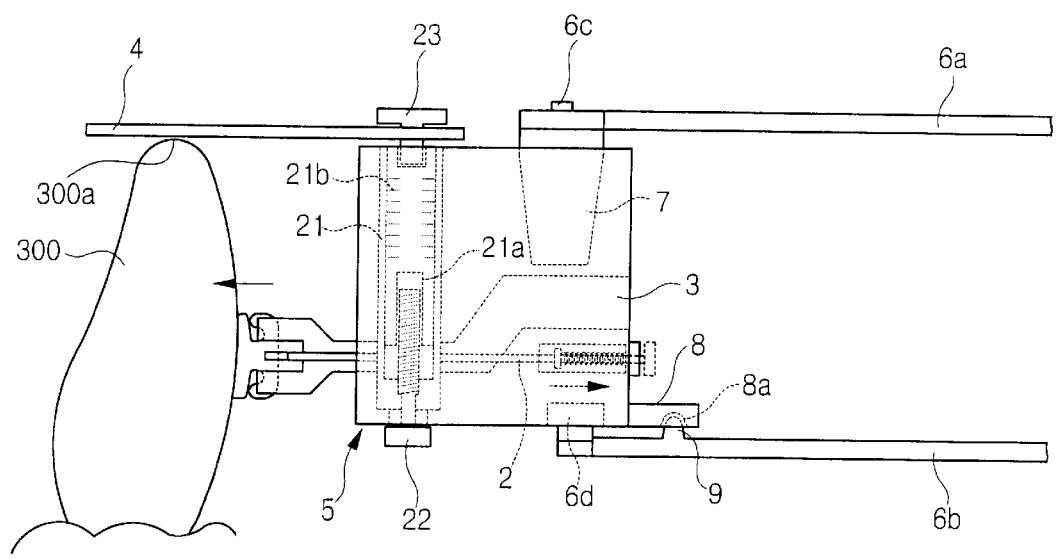
FIG. 4b is a front view showing the attachment of the brackets on the teeth using the embodiment of the present invention.
Figure 5:
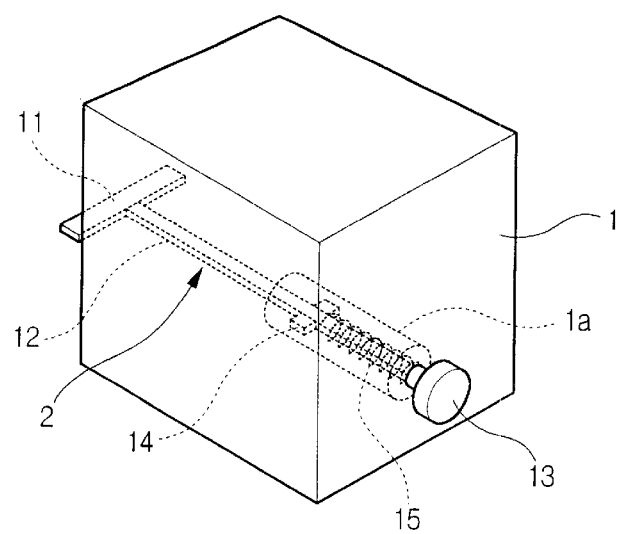
FIG. 5 is a detailed perspective view of a bracket support of the embodiment.

As shown in FIGS. 4a to 5, an orthodontic jig for attaching and positioning the brackets on the teeth according to an embodiment of the present invention comprises a housing 1 having a tube 1a extended inwardly from the back side thereof, a bracket support 2 extended out of the front side of the housing 1 through the tube 1a, tweezers 3 for gripping the tie wings of the bracket connected to the housing 1 and disposed around the bracket support 2.

Figure 1A:
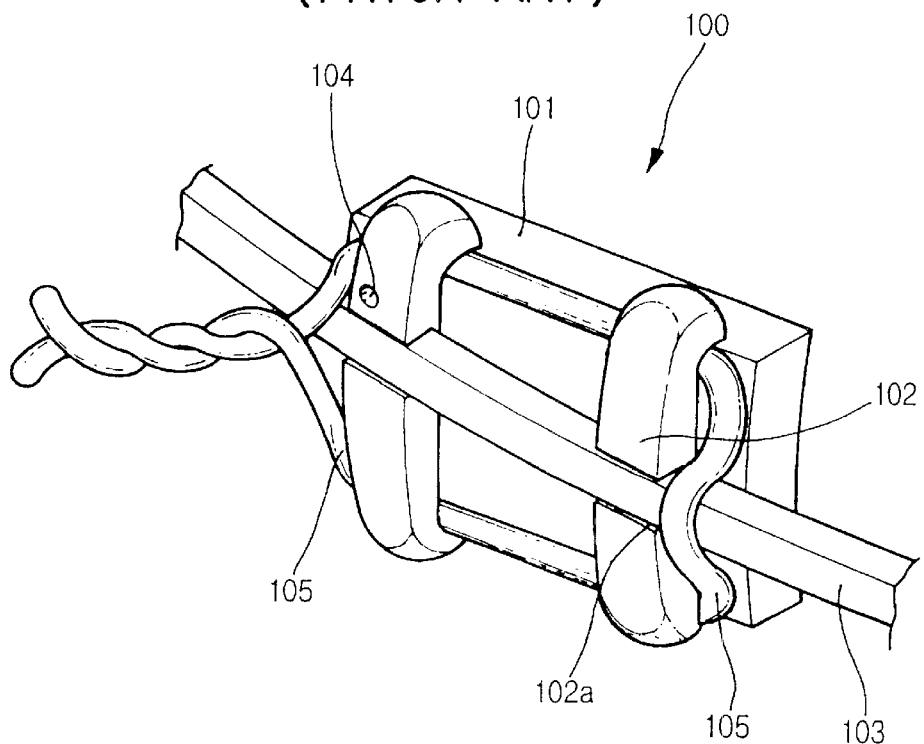
FIG. 1a is a perspective view of the structure of a common orthodontic bracket.
Figure 1B:
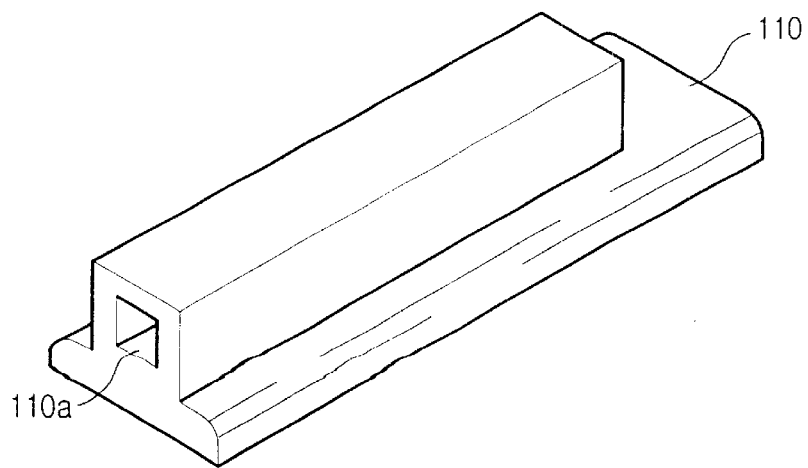
FIG. 1b is a perspective view of the structure of a common orthodontic tube.
Figure 2A:
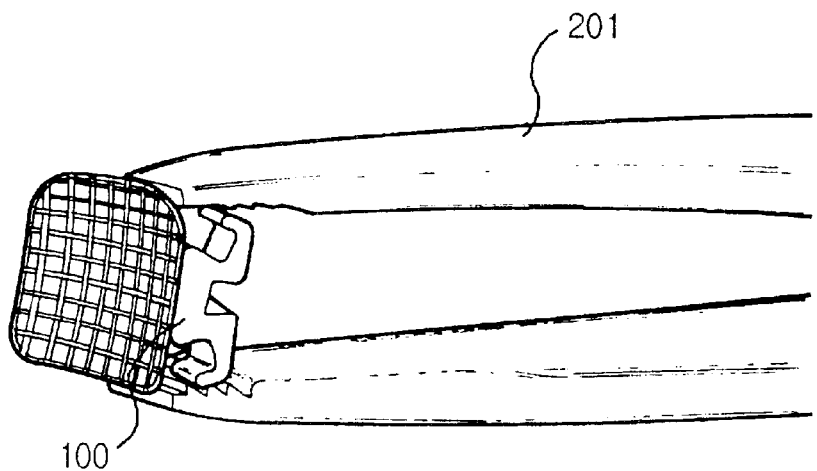
FIGS. 2a and 2b are a perspective view of the structure of a conventional tweezers.
Figure 2B:
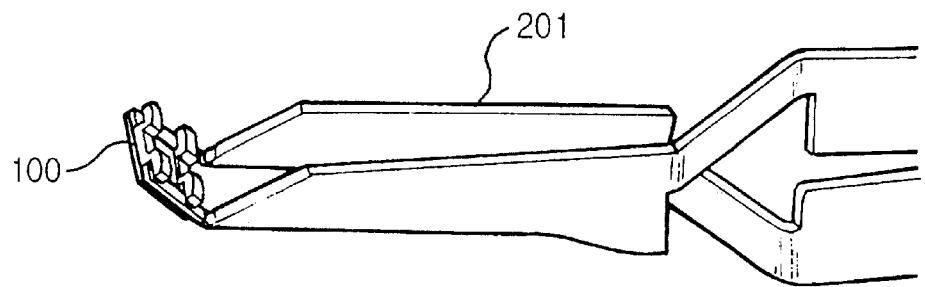
Figure 3:
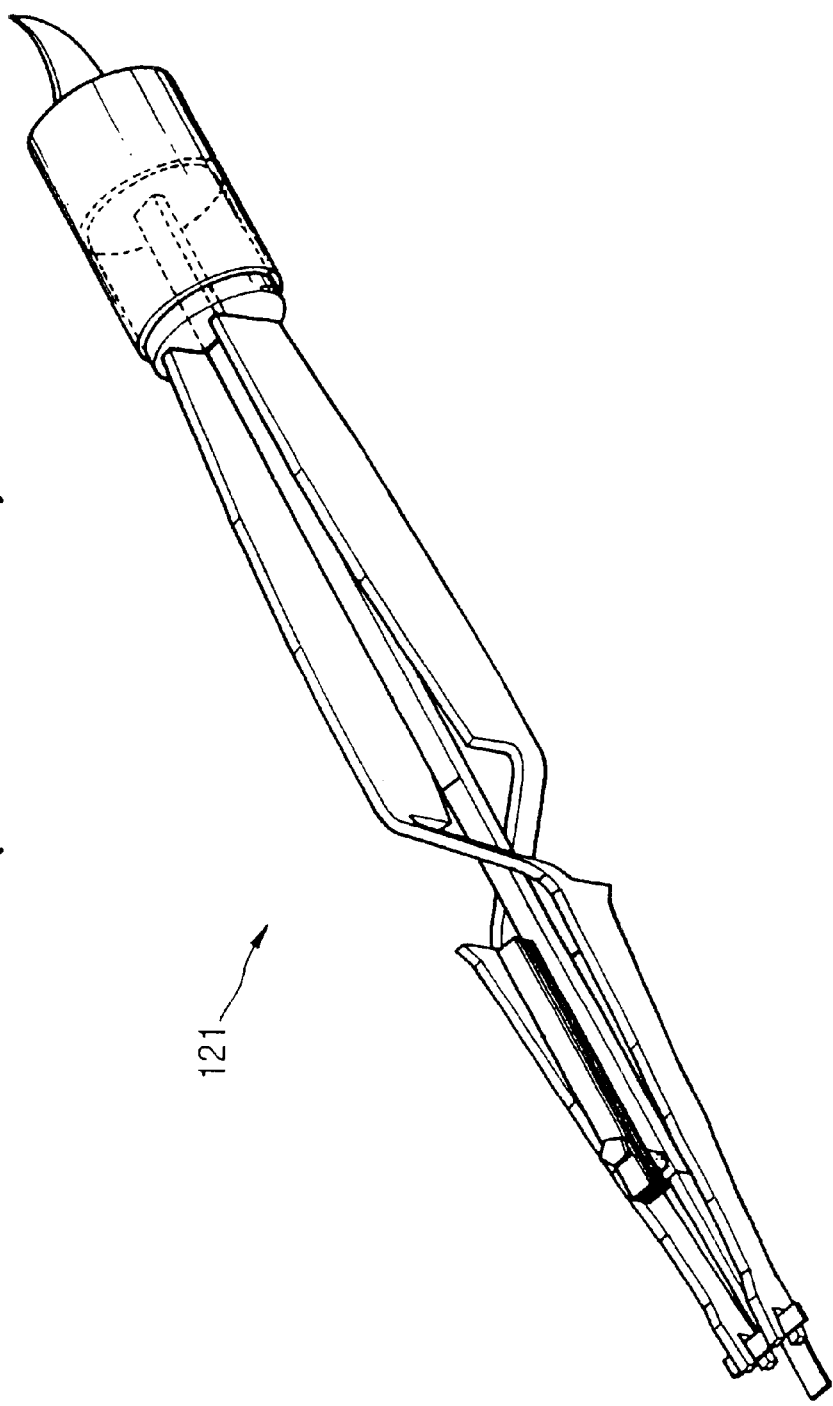
FIG. 3 is a perspective view of the structure of another conventional tweezers.

Referring to FIGS. 1 and 5, the bracket support 2 comprises a support plate 11 inserted in the slot 102a of the bracket 100, a center plate 12 inserted in the tube 1a and formed in T shape with the support plate 11, a protuberance 14 formed in the both side of center plate 12, a fastener 13 connected with the edge of the center plate 12 for preventing the center plate from deviating the housing, and a spring 15 disposed between the fastener 13 and the protuberance 14. The spring 15 provides the bracket support 2 with restoring force when the bracket gripped by the orthodontic jig is pressed on the labial surface on the tooth. Accordingly, the bracket support 2 is movable to backward and forward direction parallel to the direction of the tube 1a and is rotatable around the axis parallel to the direction of the center plate 12.

Referring to FIGS. 4a, 4b band 5, the tweezers 3 comprises a gripping body 3a connected to the back side of the housing 1 and disposed in both side of the bracket support 2, and a gripping tip 3b having a cutout, which is adapted to receive the support plate 11, in order to grip the tie wings 102 of the bracket 100.

Figure 6:
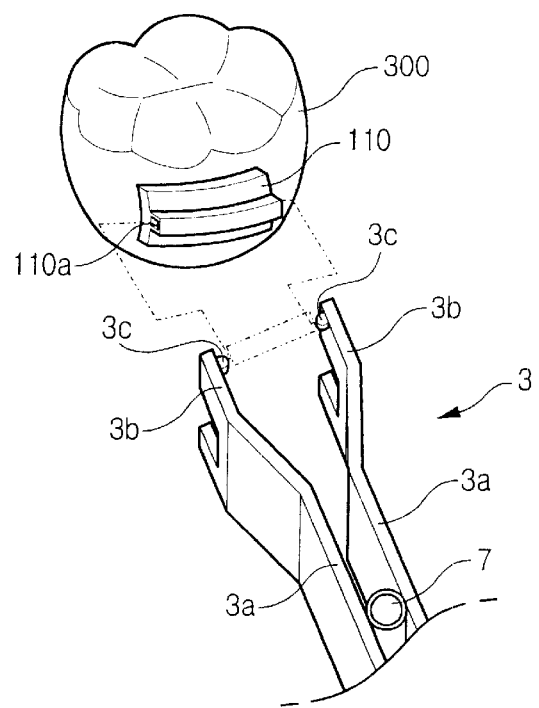
FIG. 6 is a perspective view showing the attachment of an orthodontic tube using an embodiment of the present invention.

As shown in FIG. 6, when the orthodontic tube 110 is attached on the labial surface of the molar, a hole 110a of the orthodontic tube 110 is adapted to a gripping protuberance 3c formed on the inner side of the gripping tip 3b.

Turning now to FIGS. 4a and 4b, the orthodontic jig also comprises a cusp tip reference plate 4 for setting the cusp tip 300a of the tooth 300 as the reference surface of the orthodontic position, and means 5 for displacing the cusp tip reference plate 4 upward or downward.

The displacing means 5 includes a height gauge 21 having an internal thread 21a therein and a scale 21b spaced a predetermined interval, e.g., 0.25 mm, and a height adjusting screw 22, connected to the internal thread 21a, for adjusting the vertical displacement of the height gauge 21. A pin 23 connects the cusp tip reference plate 4 with the displacing means 5. A guide tube 24 inwardly formed on the top surface of the housing 1 is parallel to the height gauge 21 and a sliding bar 25, which is connected with the cusp tip reference plate 4, is inserted into the guide tube 24. Accordingly, when the height adjusting screw 22 is rotated, the internal thread 21a is displaced up and down a predetermined pitch and then the sliding bar 25 is simultaneously displaced up and down the guide tube 24 in order to move the cusp tip reference plate 4 up and down accurately. A handle 6 having an upper plate 6a and a lower plate 6b is connected to the upper and lower surface of housing 1 by a tapered anchor 7 and a pivot pin 6d respectively. The tapered anchor 7 is connected to the bottom surface of the upper plate 6a by a fixing pin 6c. When the handle 6 is pressed, the tapered anchor 7 is inserted into the tweezers 3 and then the span of the tweezers 3, which is equal to the diameter of the tapered anchor 7, is enlarged so that the gripping tip 3b grips the tie wings 102 of the bracket.

Figure 10:
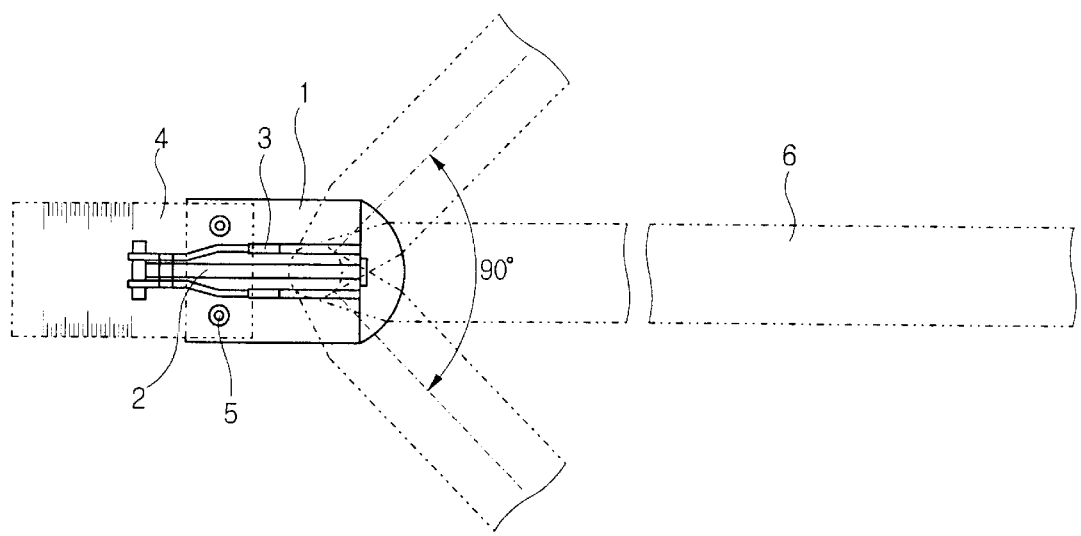
FIG. 10 is a plan view showing the rotation operation of a handle of the embodiment.

Referring to FIGS. 4a to 4b and FIG. 10, the housing 1 comprises a handle positioning plate 8 having positioning recesses 8a spaced with 22.5° at the arc shaped bottom surface thereof. The handle 6 is rotated around the pivot pin 6d and one of the positioning recess 8a is fitted with a positioning protuberance 9 formed on the lower plate 6b so that an angle between the tweezers 3 and the handle 6 is set within 45° to the left side and the right side respectively.

The operation of the orthodontic jig according to the embodiment of the present invention is as follows.

Figure 7:
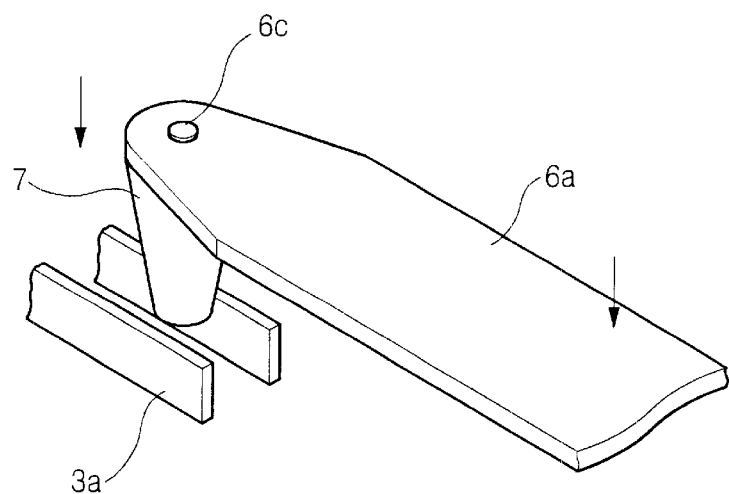
FIG. 7 is a fragmentary perspective view showing the gripping operation of the bracket support of the embodiment.

When the upper plate 6a and the lower plate 6b of the handle 6 are pressed, as shown in FIG. 7, the tapered anchor 7 is inserted into the tweezers 3 and then the span of the tweezers 3 is enlarged so that the gripping tip 3b may grip the tie wings 102 of the bracket. Also, the support plate 11 disposed in the cutout is inserted into the slot 102a of the bracket 100. When the handle 6 is released, the anchor 7 is ascended from the gripping body 3a, and therefore the space between the gripping tips 3b is reduced and the gripping tip 3b grips the tie wings 102 of the bracket 100.

Figure 8A:
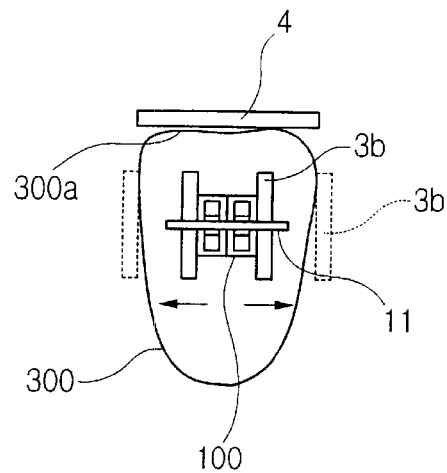
FIG. 8a is a front view showing the bracket attached on the tooth using the embodiment.
Figure 9:
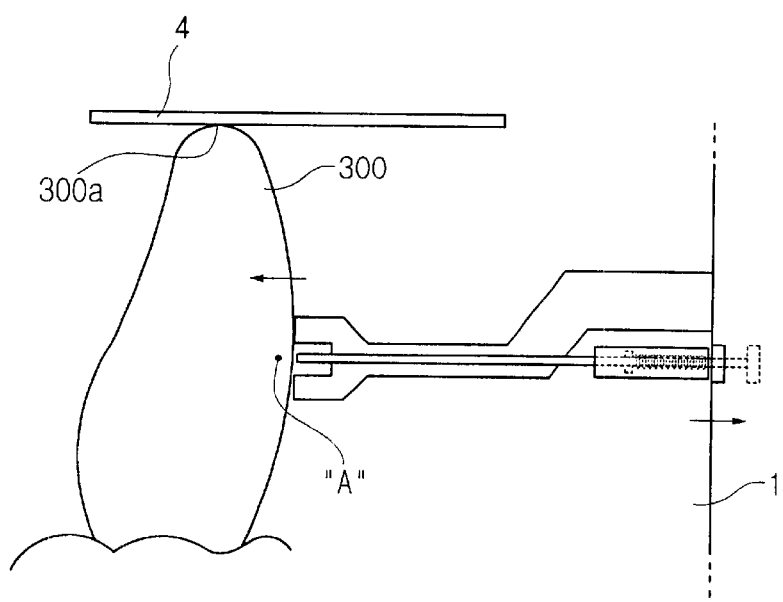
FIG. 9 is a fragmentary side view showing the pressing operation of the bracket support of the embodiment.

The bracket 100 gripped by the orthodontic jig, as shown in FIG. 4b and FIG. 9, is contacted on the labial surface of the tooth and the cusp tip reference plate 4 is contacted on the cusp tip 300a of the tooth 300. As the height adjusting screw 22 is rotated to the clockwise or counter-clockwise direction, the height gauge 21 is moved up and down, so that the height between the cusp tip reference plate 4 and the bracket 100 may be calibrated and the orthodontic position 'A' may be set. The orthodontist can adjust the orthodontic position 'A' by reading the scale 21b. And then the adhesive is coated on the bottom surface of the bracket 100 and the bracket 100 is adhered to the labial surface of the tooth through the same procedure setting the orthodontic position 'A'. In order to adhere the bracket to the tooth firmly, the gripping tip 3b is pressed forward and then the bracket support 2 is moved backward and the compression force of the spring 15 press the bracket 100 onto the tooth. After the adhesion of the bracket 100 is completed, as shown in FIG. 7 and FIG. 8a, the lower plate 6b of the handle 6 are pressed, the tapered anchor 7 is inserted into the tweezers 3 and then the gripping tip 3b is released.

Figure 8B:
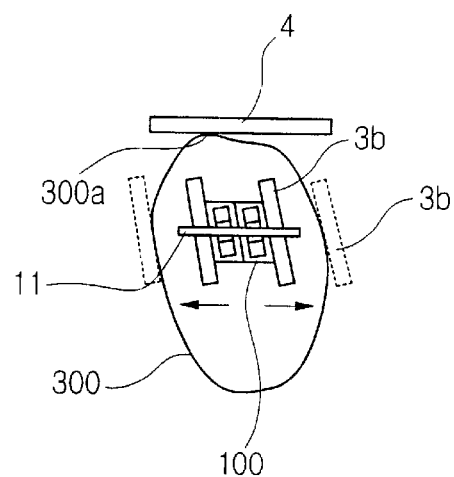
FIG. 8b is a front view showing the bracket provided with angulation on the tooth using the embodiment.

Referring to FIG. 8b, when the tooth has some angulation, the bracket 100 must be attached with the same angulation as the tooth. In this case, the support plate 11 of the bracket support 2 is rotated within the cutout and inserted into the inclined slot of the bracket 100. The attachment of the bracket having a inclined slot on the tooth is substantially the same as the above procedure.

Figure 11:
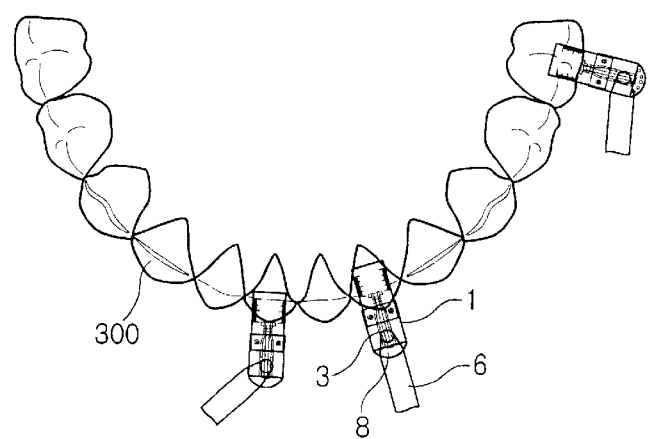
FIG. 11 is a plan view showing the various position of the handle according to the position of the teeth.

Referring to FIGS. 10 and 11, when the bracket is attached on the molar, the handle 6 is angled with the tweezers 3 within 45° so that the front surface of the housing 1 faces with the labial surface of the molar. That is, as shown in FIGS. 4a, 4b and 11, the handle 6 is rotated around the pivot pin 6d to angle with the housing 1 within 90° and one of the positioning recess 8a is fitted into the positioning protuberance 9 on the lower plate 6b, so that the orthodontist can attach the bracket on the molar with ease.

Figure 12:
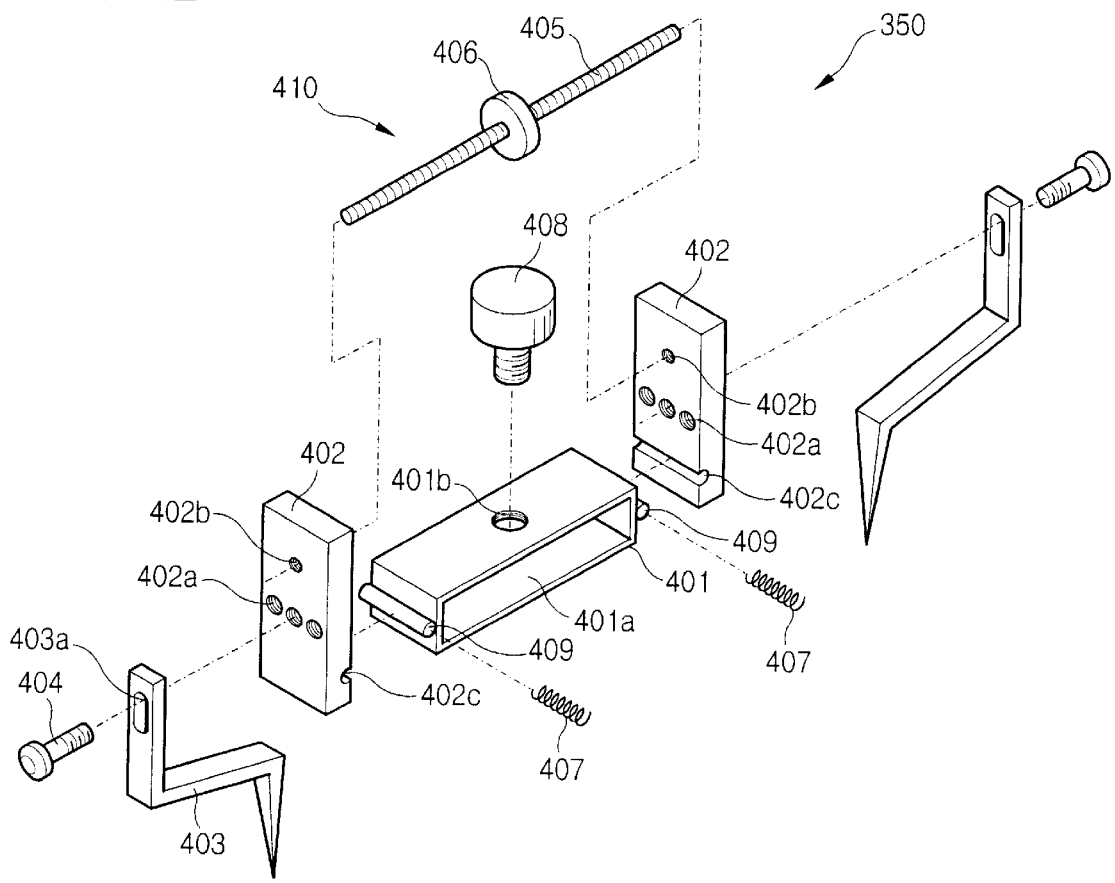
FIG. 12 is an exploded perspective view showing a first embodiment of an occlusal fossa positioning device coupling to the orthodontic jig.
Figure 13:
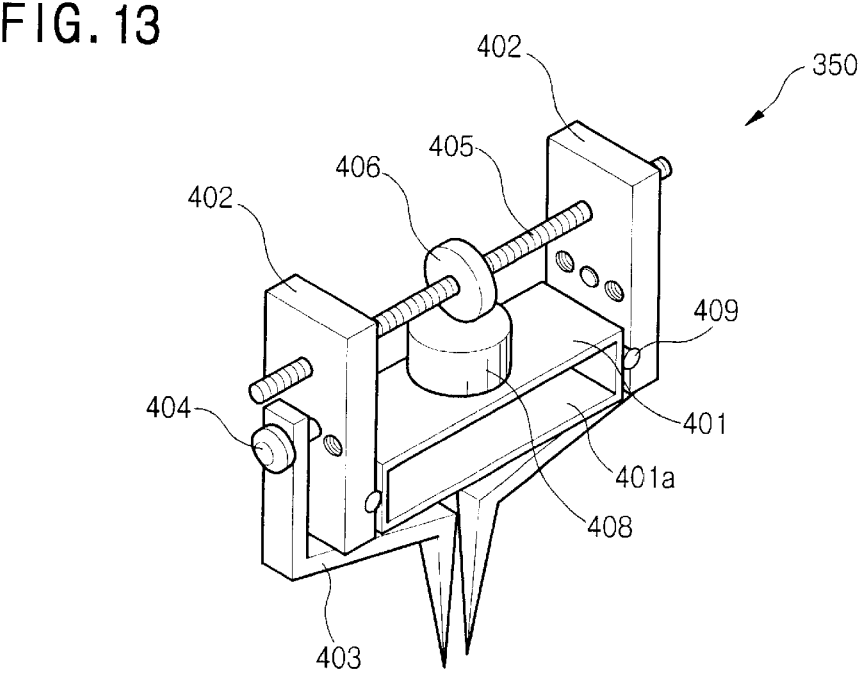
FIG. 13 is a perspective view of the first embodiment of the occlusal fossa positioning device.
Figure 14:
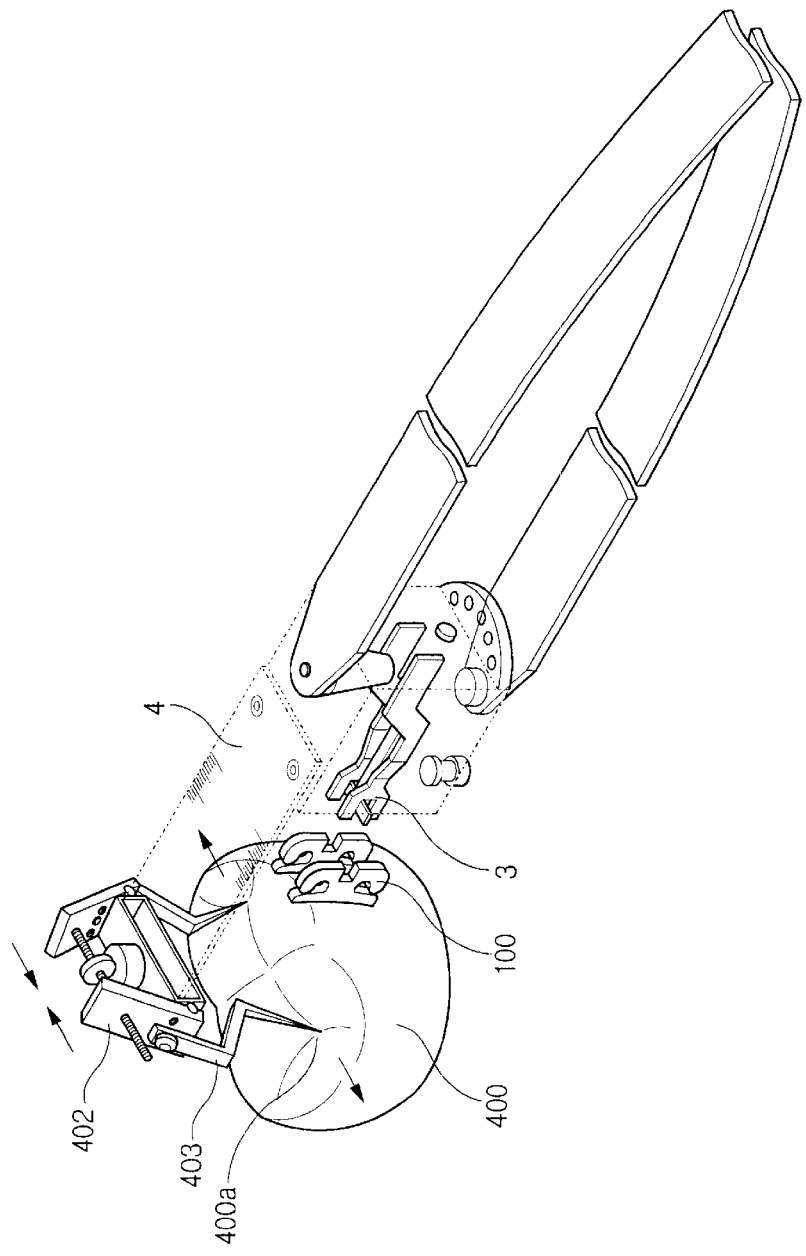
FIG. 14 is a perspective view showing the positioning operation of the bracket on the tooth with the orthodontic jig coupled to the occlusial fossa positioning device.

The orthodontic jig may be connected with an occlusal fossae positioning device in order to correct the misaligned teeth having angulation, torque, rotation and height difference more accurately. A first embodiment of the occlusal fossae positioning device is shown in FIGS. 12 to 14 and is designated by the reference number 350. The occlusal fossae positioning device 350 comprises a frame 401 having a connecting rod 409 and a channel 401a connected with the cusp tip reference plate 4 by the fastener 408 through an opening 401b, panels 402, disposed at each side of the frame 401, having a plurality of holes 402a, upper holes 402b and grooves 402c fitted with the connecting rod 409, an occlusal fossae positioning pin 403 connected with the panel 402 by a fastener 404 through a vertically elongated hole 403a and one of the holes 402a, and a span adjusting screw 410 inserted into the upper holes 402b for adjusting the span between the panels 402.

The span adjusting screw 401 comprises an external thread rods 405 connected to the upper holes 402b and a span adjusting disc 406, disposed between the external thread rods 405, for varying the span of the panels 402 by its rotation. As each internal thread of upper holes 402b is formed at the opposite direction, the panels can move inwardly or outwardly by the rotation of the span adjusting disc 406.

The operation of the orthodontic jig connected with a first embodiment of the occlusal fossae positioning device 350 is as follows.

Referring to FIG. 14, the occlusal fossae positioning device 350 is adapted to receive the cusp tip reference plate 4 and the tweezers 3 connected with the cusp tip reference plate 4 grips the bracket. And then the edge of occlusal fossae positioning pin 403 is positioned at the occlusal fossae 400a of the molar 400. In this case, since each person or each molar has a different size, the span between the edges of occlusal fossae positioning pins 403 must be adjusted. As the span adjusting disc 406 is rotated, the span between the upper portions of panels 402 is reduced in FIG. 14 (or enlarged), and the panels 402 is pivoted around the connecting rod 409, so that the span between the edges of occlusal fossae positioning pins 403 is enlarged in FIG. 14 (or reduced). Springs 407 inserted into the grooves 402 provide the panels 402 with the restoration force.

When the molar has some torque, rotation, or angulation representing the inclination θ' toward the labial side or the tongue side, the amount of twist around the molar axis, or the inclination toward an adjacent tooth respectively, the occlusal fossae positioning pin 403 can be connected with the proper one of the holes 402a and the height thereof can be very accurately adjusted with varying the connection position of the elongated hole 403a. Accordingly, the attaching position of the bracket is set according to the torque, rotation and angluation of the molar so that the malocclusion of the teeth can be corrected ideally.

Figure 15:
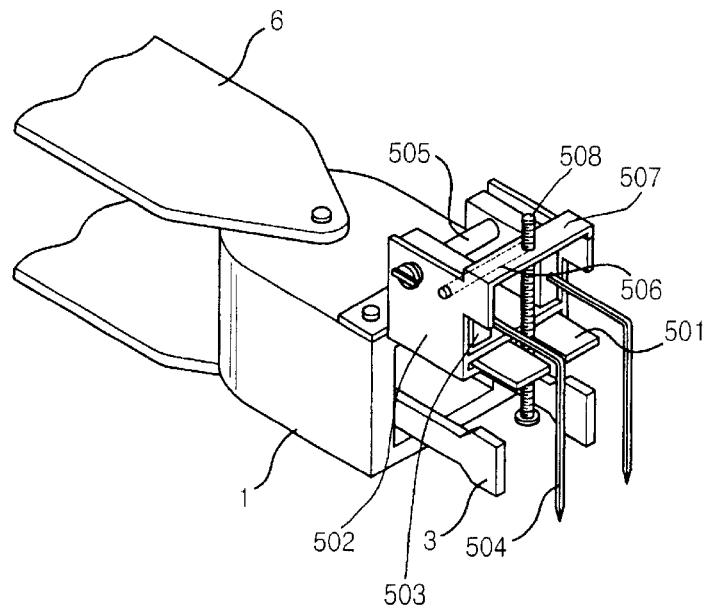
FIG. 15 is a perspective view of a second embodiment of the occlusal fossa positioning device coupled to the orthodontic jig.
Figure 16:
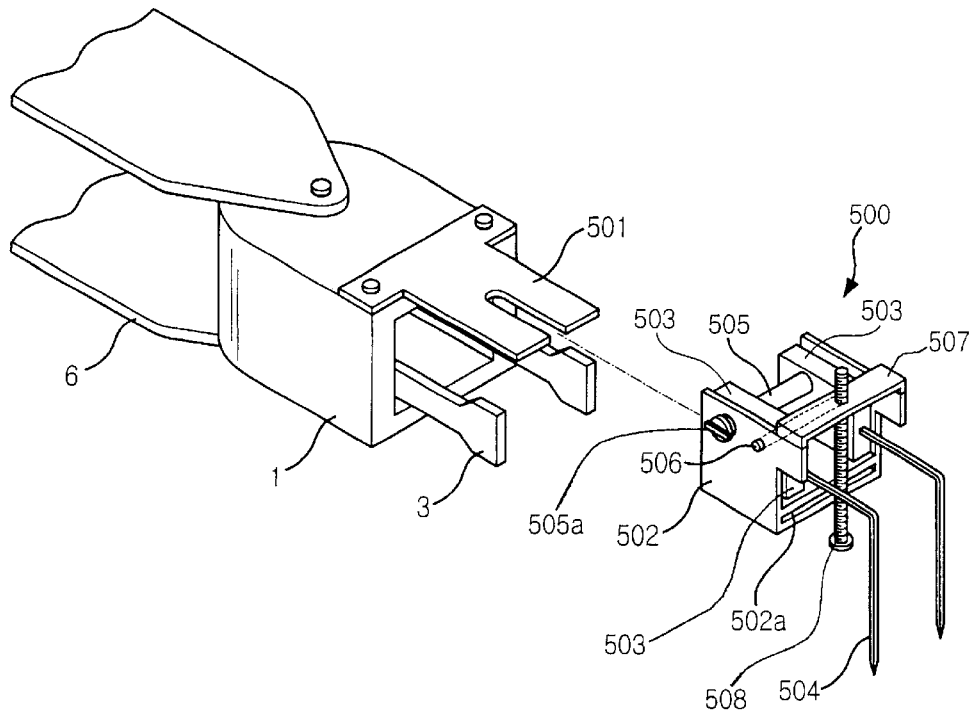
FIG. 16 is a perspective view of the second embodiment of the occlusal fossa positioning device separated from the orthodontic jig.

Referring now to FIGS. 15 and 16, there is shown a second embodiment of the occlusal fossae positioning device. The second embodiment illustrated in FIGS. 15 and 16, that is, the occlusal fossae positioning device 500 is, in all major aspect, substantially the same as the first embodiment in FIGS. 10 to 13 and will not be described in detail. However, in the second embodiment, the cusp tip reference plate 501 is provided with a cutout which provides a reference adjusting rod 508 with the moving space. The occlusal fossae positioning device 500 comprises a frame body 502 having a channel 502a connected with the cusp tip reference plate 501, panels 503 disposed at each inner side of the frame body 502, an occlusal fossae positioning pin 504 connected with the panel 503, a span adjusting screw 505 connected through the both sides of the frame body 502 and the panels 503 for adjusting the span between the panels 503, a sliding guide pin parallel to the span adjusting screw 505 for guiding the panels 503 outwardly or inwardly, and a reference adjusting rod 508 connected through the upper surface of the frame body 502.

The reference adjusting screw 505 is rotated to come in contact with the upper surface of the molar, a handle 505a of the span adjusting screw 505 is rotated so as to adjust the span between the panels 503 and then the occlusal fossae positioning pin 504 comes in contact with two occlusal fossae of the molar. Other procedure of the attachment of the bracket to the labial surface of the molar is substantially the same as the first embodiment in FIGS. 10 to 13 and will not be described in detail.

Figure 17:
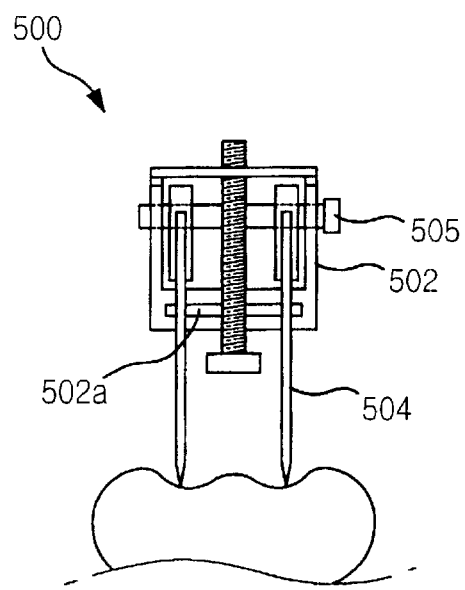
FIG. 17 is a front view of the second embodiment of the occlusal fossa positioning device.
Figure 18:
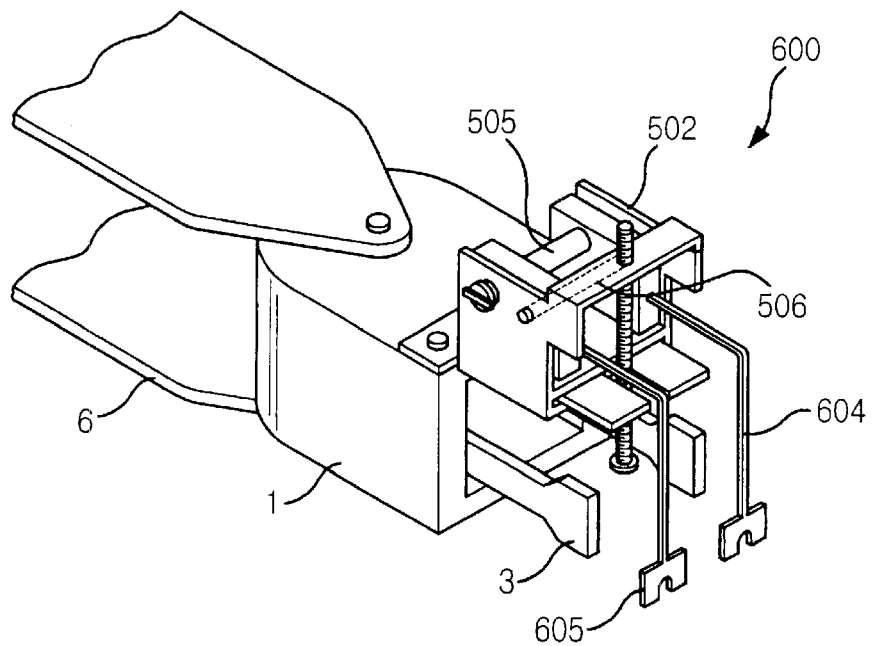
FIG. 18 is a side view of a third embodiment of the occlusal fossa positioning device coupled to the orthodontic jig.
Figure 19:
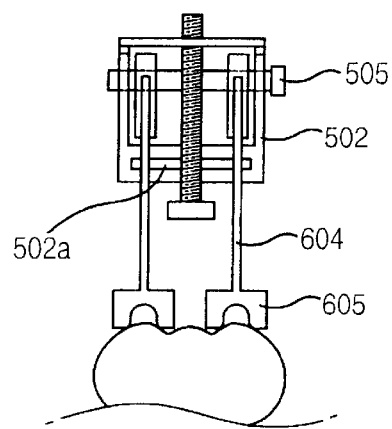
FIG. 19 is a front view of the third embodiment of the occlusal fossa positioning device.

FIGS. 18 and 19 illustrate a third embodiment of the occlusal fossae positioning device. The third embodiment, that is, the occlusal fossae positioning device 600 is, in all major aspect, substantially the same as the second embodiment in FIGS. 15 to 17 but that the edge of the occlusal fossae positioning pin includes a positioning plate 605.

Figure 20:
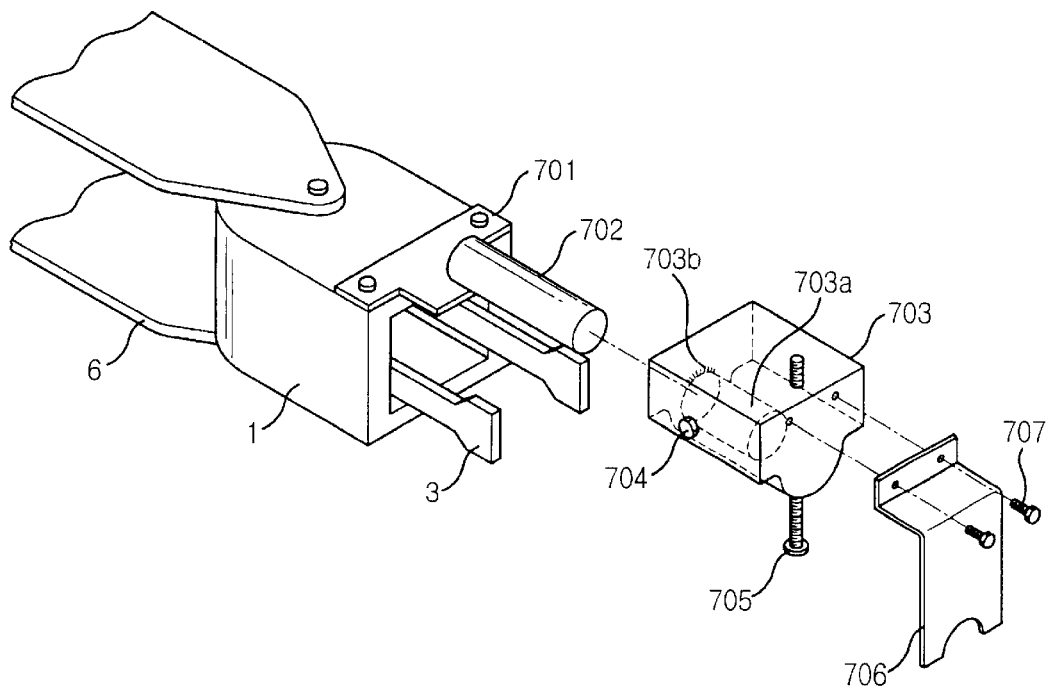
FIG. 20 is an exploded perspective view of a fourth embodiment of the occlusal fossa positioning device separated from the orthodontic jig.
Figure 21:
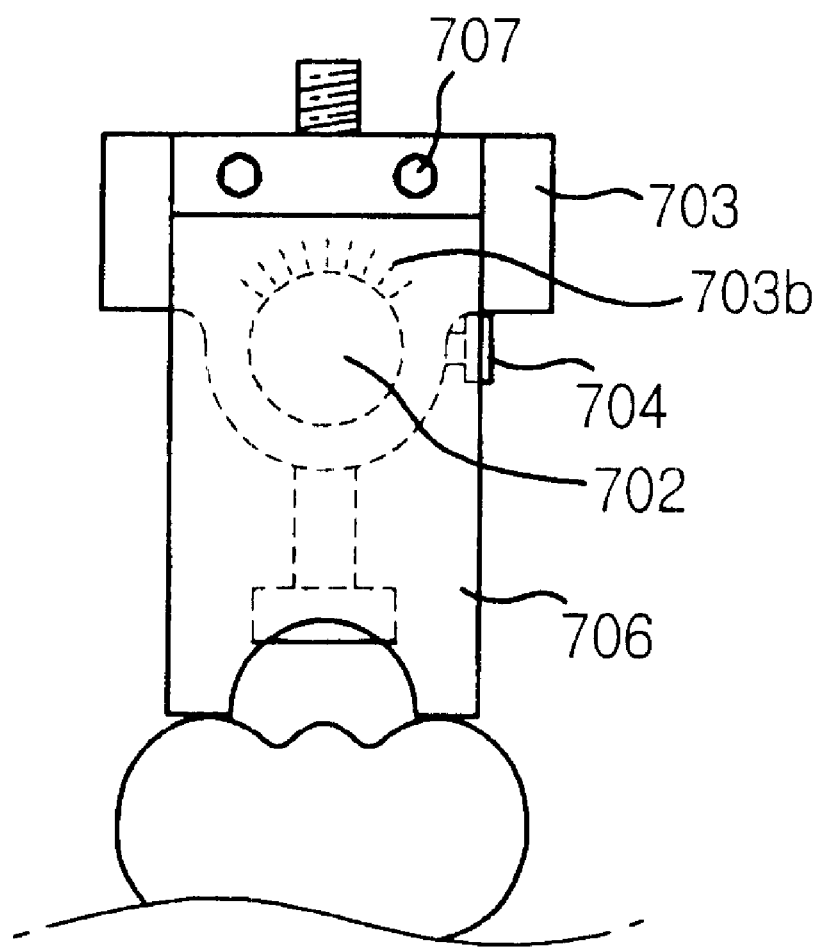
FIG. 21 is a front view of the fourth embodiment of the occlusal fossa positioning device.

FIGS. 20 and 21 illustrate a fourth embodiment of the occlusal fossae positioning device. The fourth embodiment comprises a reference rod 702 mounted on the cusp tip reference plate 701, a frame body 703 having a cylindrical hole 703a connected with the cusp tip reference rod 702 by a fastener 704 and a scale 703b formed on the peripheral portion around the cylindrical hole 703a, a reference adjusting rod 705 connected through the upper surface of the frame body 703, an occlusal fossae positioning plate 706 connected with the frame body 703.

Referring to FIGS. 20 and 21, the height of the cusp tip reference plate 701 is adjusted by the height gauge so that the bracket may be positioned at the accurate orthodontic position and the occlusal fossae positioning plate 706 may be contacted on the occlusal surface. And then the reference adjusting rod is positioned on the occlusal surface. When the molar has some torque, rotation or angulation, the frame body 703 is rotated around the reference rod 702, with reading the scale 703b. And then the bracket is attached on the labial surface of the molar as described in the above.

Figure 22:
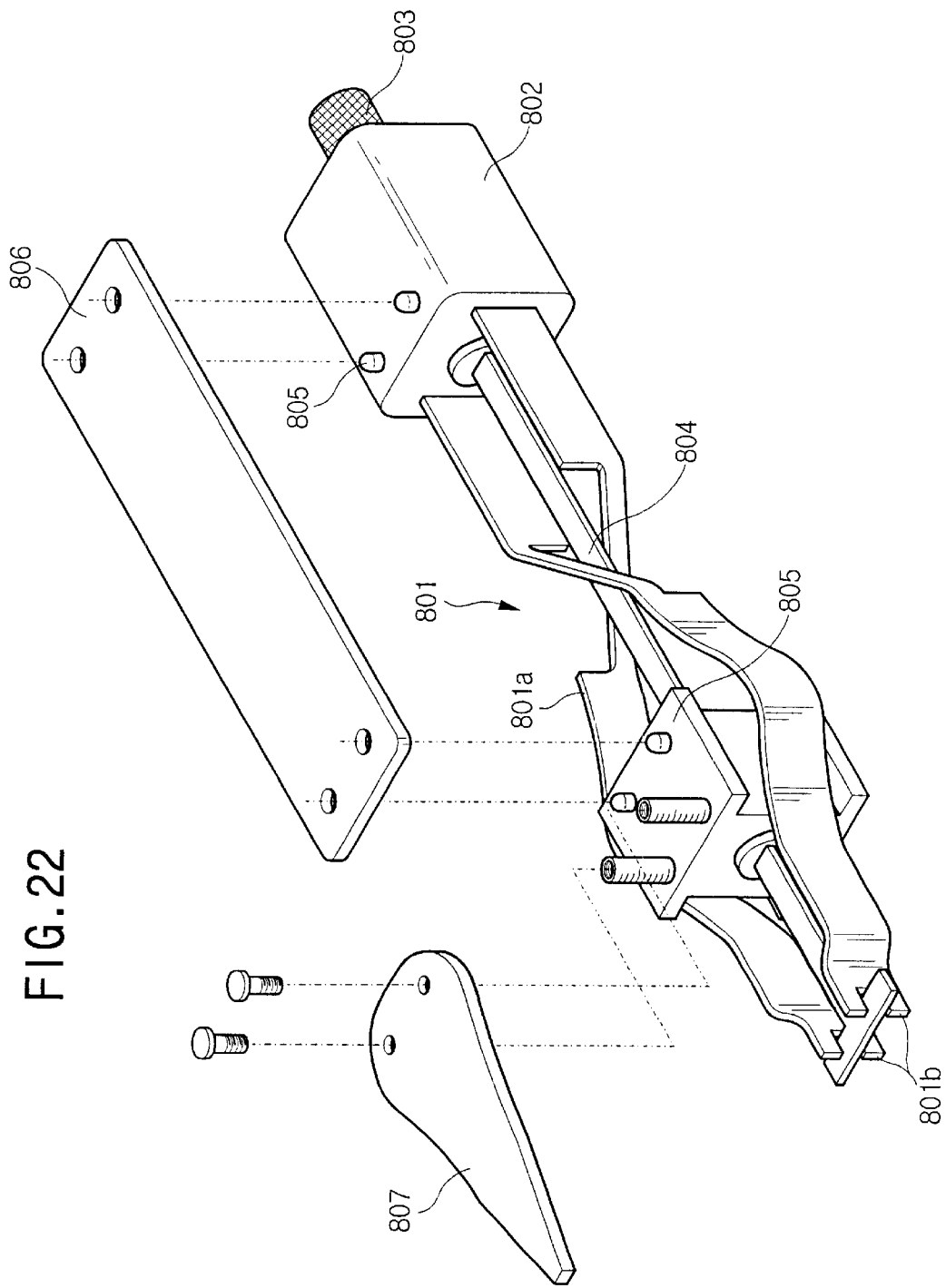
FIG. 22 is a perspective view of the orthodontic jig for attaching and position brackets according to another embodiment of the present invention.

FIG. 22 illustrates an orthodontic jig according to a modification of the present invention which gives the simpler structure of the cusp tip reference plate and the bracket support. In the orthodontic jig of FIG. 22, tweezers 801 comprises two cross over extended parts 801 which are provided with a gripping tip 801b to grip the tie wing of the labial bracket 100. The housing includes a tweezers support 802 and a height gauge 805. The tweezers support 802 is connected with the edge of the tweezers 801. The height gauge 805 is disposed between the extended parts 801a and is connected with the height adjusting screw and is moved up and down with the sliding bar. The bracket support 804 is inserted through the housing, one edge of the bracket support is formed with 'T' shape and the other edge of the bracket support includes a rotation adjusting handle 803. The cusp tip reference plate 807, which set the orthodontic position of the bracket from the cusp tip of the tooth, is fixed with the upper edge of the height gauge. A fixing plate 806 connects the height gauge 805 with the tweezers support 802 so as to prevent the height gauge 805 from fluctuating up and down.

The operation of another embodiment is substantially similar to the above. That is, the bracket 100 gripped by the orthodontic jig is contacted on the labial surface of the tooth and the cusp tip reference plate 807 is contacted on the cusp tip of the tooth. As the height adjusting screw is rotated to the clockwise or counter-clockwise direction, the height gauge 805 is moved up and down, so that the height between the cusp tip reference plate 807 and the bracket may be calibrated and the orthodontic position 'A' may be set. The orthodontist can adjust the orthodontic position 'A' by reading the scale. And then the adhesive is coated on the bottom surface of the bracket 100 and the bracket 100 gripped by the orthodontic jig is contacted and adhered to the labial surface of the tooth through the same procedure setting the orthodontic position.

Meanwhile, the orthodontic jig of the present invention may further comprise a lingual bracket positioning device.

Figure 23A:
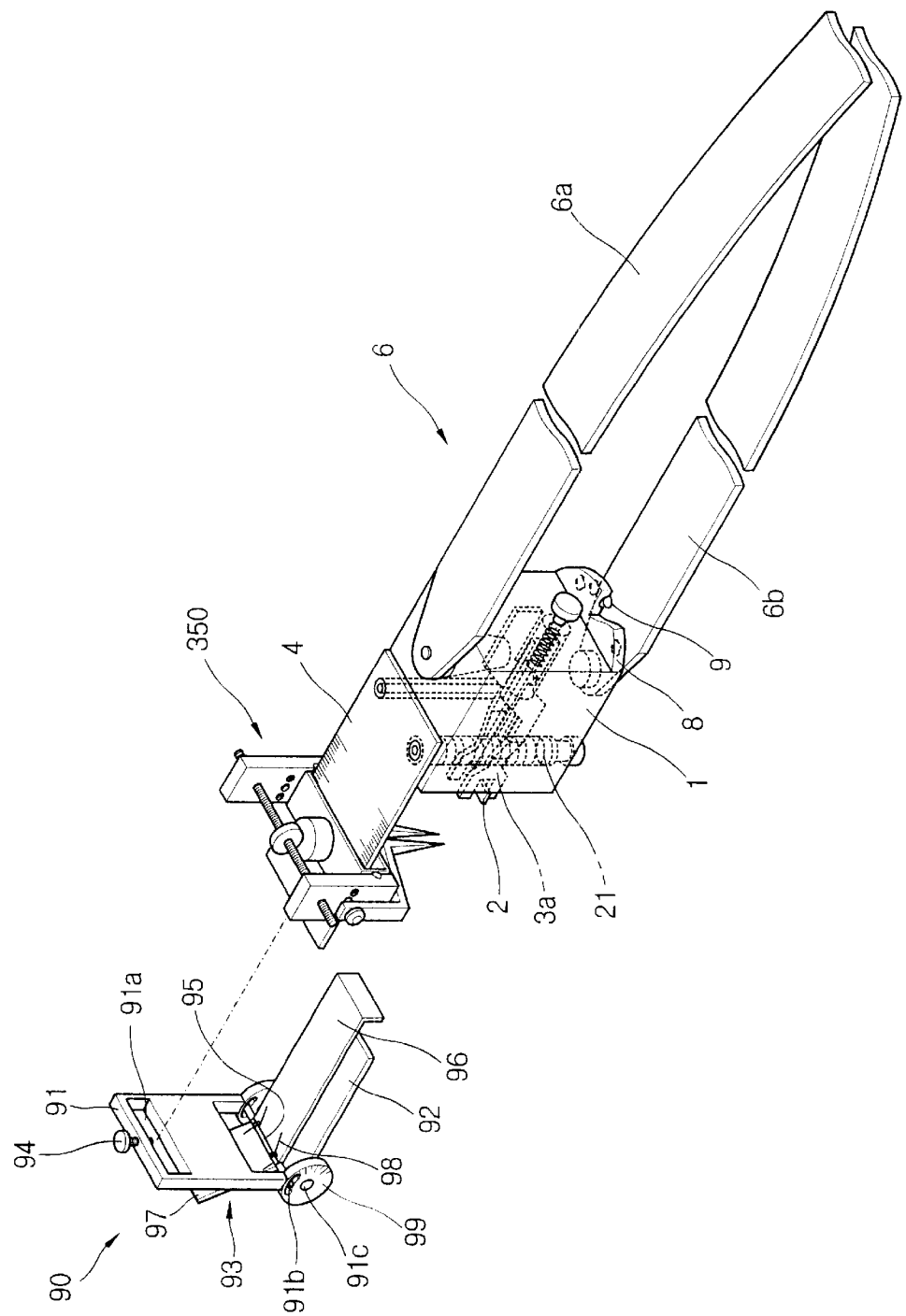
FIG. 23a is a perspective view of an embodiment of the orthodontic device for attaching a labial bracket coupled to the orthodontic jig.
Figure 23B:
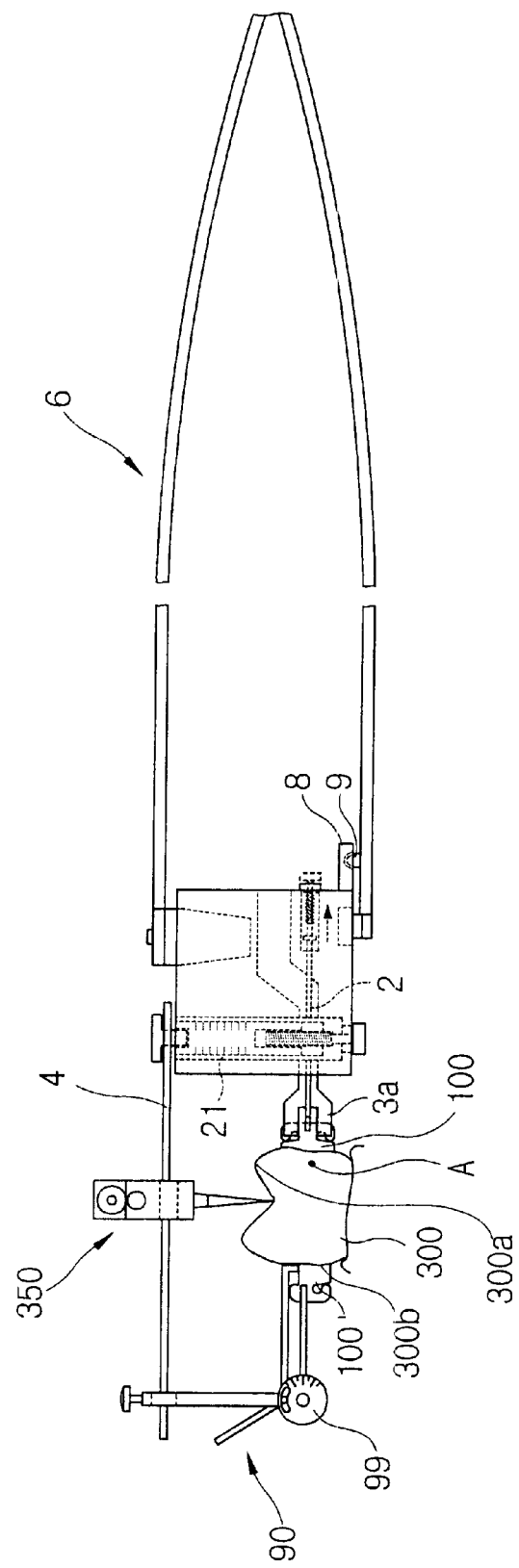
FIG. 23b is a side view of the embodiment of the orthodontic device for attaching a labial bracket coupled to the orthodontic jig.
Figure 24A:
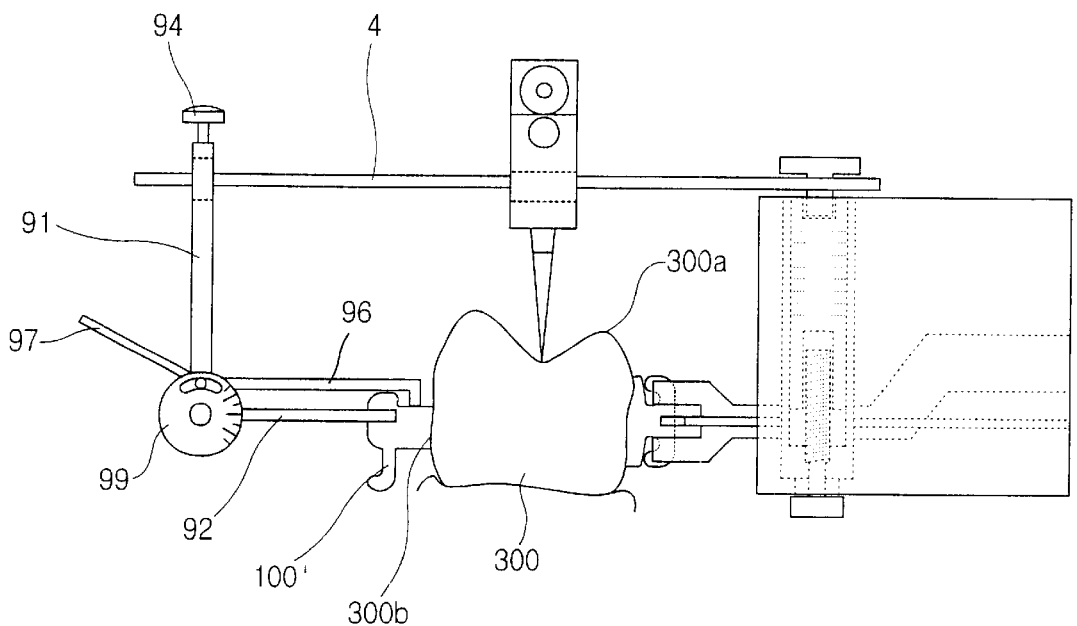
FIGS. 24a to 24c are a side view showing the attachment of the labial bracket on the tooth using the orthodontic jig connected with the embodiment.
Figure 24B:
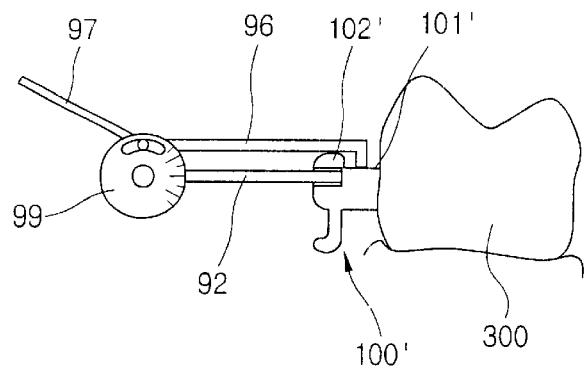
Figure 24C:
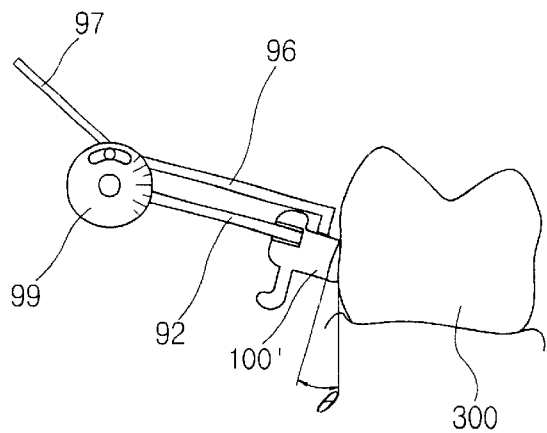

Referring to FIGS. 23a and 23b, the lingual bracket positioning device 90 comprises a vertical frame 91, a lingual bracket support plate 92 inserted into the slot of the lingual bracket, and a lingual bracket tweezers 93 connected to the vertical frame 91 for gripping the tie wings of the lingual bracket. The vertical panel 91 is provided with a hole 91a connected to the cusp tip reference plate 4, a scale disc 99 provided with an elongated hole 91b formed on a concentric circle and a connecting hole 91c connected to the lingual bracket support plate 92 at the center of the disc. The lingual bracket tweezers 93 are provided with a tie wing gripping panel 96 for gripping the tie wings of the lingual bracket, a pressing panel 97 for pivoting the wing gripping panel 96, a connecting pin 95 connected to the wing gripping panel 96 and the pressing panel and inserted into the elongated hole 91b and a spring 98 for providing the bracket support plate 92 with the restoration force.

The operation of the orthodontic jig connected with the lingual bracket positioning device is as follows.

When the handle 6 are pressed, as shown in FIGS. 23a to 23c, the tapered anchor is inserted into the tweezers and then the span of the tweezers is enlarged so that the gripping tip 3b may grip the tie wings of the labial bracket 100. Also, the support plate 11 disposed in the cutout is inserted into the slot of the labial bracket 100. When the handle 6 is released, the anchor is ascended from the gripping body 3a, and therefore the space between the gripping tips 3b is reduced and the gripping tip 3b grips the tie wings of the labial bracket 100. The labial bracket 100 gripped by the orthodontic jig is contacted on the labial surface of the tooth. As the height adjusting screw 22 is rotated so that the height gauge 21 is moved up and down, the height between the cusp tip reference plate 4 and the bracket 100 is calibrated. The occlusal fossae positioning pin 403 is positioned on two occlusal fossae of the molar 300.

Also, the ligual bracket 100' gripped by the lingual bracket positioning device is positioned on the lingual surface of the molar. The height of the lingual bracket 100' is also adjusted by the rotation of the height adjusting screw 22. As the pressing panel 97 of the lingual bracket tweezers 93 is pressed, the wing gripping panel 96 is rotated upward. The bracket support plate 92 is inserted into the lingual bracket 100' and, the wing gripping panel 96 is restored by releasing the pressing panel 97, so that the tie wings of the lingual bracket 100' is gripped by the wing gripping panel 96 and the orthodontic position of the lingual bracket 100' is set. And then the adhesive is coated on the bottom surface of the lingual bracket 100' and the lingual bracket 100' is adhered to the lingual surface of the molar through the same procedure setting the orthodontic position.

When the molar has torque θ' toward the labial side or the tongue side, the bracket support plate 92 is rotated within the elongated hole 91b with reading the scale disc 99 and then the lingual bracket 100' is gripped by the lingual bracket tweezers. The lingual bracket 100' is adhered to the lingual surface of the molar through the same procedure.

In order to attach the lingual bracket 100' on the lingual surface of the incisor, the orthodontic jig must be connected only with the lingual bracket positioning device and without the occlusal fossae positioning device.

Figure 25:
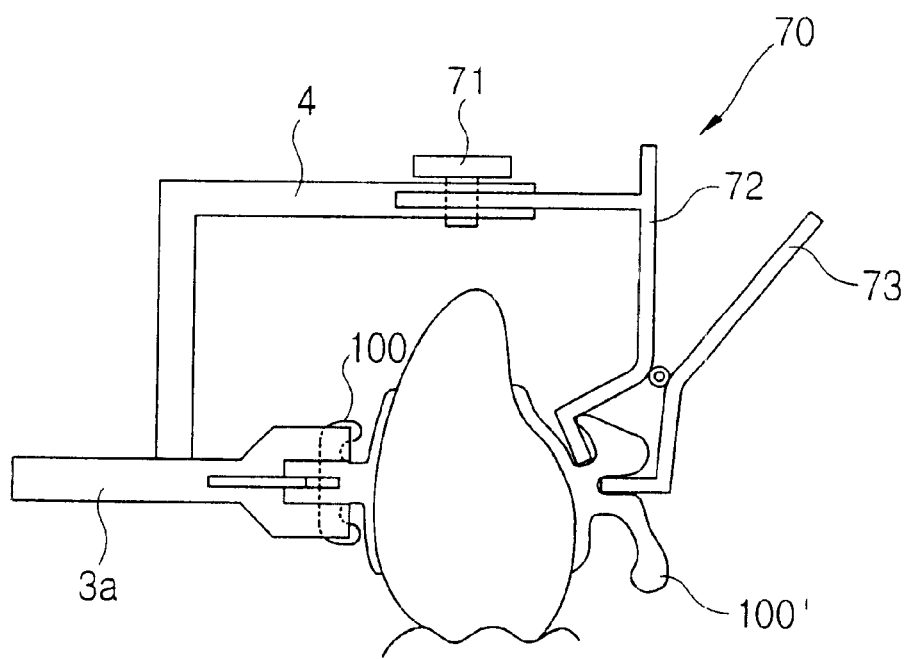
FIG. 25 is a side view of another embodiment of the orthodontic device for attaching a labial bracket.

FIG. 25 illustrates another embodiment of the lingual bracket positioning device. The lingual bracket positioning device comprises a wing gripping panel 72 connected with the cusp tip reference plate 4 by the fastener 71 for gripping the tie wing of the lingual bracket 100', a clamp 73 pivotally connected with the wing gripping panel 72 for gripping any part of the lingual bracket 100' (for example, the slot or another tie wing of the lingual bracket 100').

There have been disclosed heretofore the best embodiments of the invention presently contemplated. However, it is to be understood that various changes and modifications may be made thereto without departing from the spirit of the invention.

What is claimed is:

1. An orthodontic jig for positioning an orthodontic bracket comprising:
    a housing;
    a bracket support extending out of a front side of the housing through a back side of the housing;
    tweezers for gripping tie wings of the bracket connected to the housing and disposed around the bracket support, wherein the tweezers comprise:
        a gripping body connected to the back side of the housing and disposed in both sides of the bracket support; and
        a gripping tip including a cutout for gripping the view wings of the bracket;
    a cusp tip reference means for setting a cusp tip of the tooth as a reference surface of the orthodontic position;
    means for displacing a cusp tip reference plate upward or downward; and
    a handle connected to upper and lower surfaces of the housing for supporting the housing.

2. An orthodontic jig according to claim 1, wherein the bracket comprises:
    a support plate for insertion in a slot of the bracket;
    a center plate formed in T-shape with the support plate and extended through the housing;
    a fastener connected with a center plate for preventing the center plate from deviating the housing; and
    a spring disposed between the fastener and a protuberance for providing the bracket support with restoring force.

3. An orthodontic jig according to claim 1, the tweezers comprises
    gripping body connected to the back side of the housing and disposed in both side of the bracket support; and
    gripping tip including a cutout for gripping the tie wings of the bracket.

4. An orthodontic jig according to claim 3, wherein the gripping tip further comprises a protuberance on an inner side thereof.

5. An orthodontic jig according to claim 1, wherein the displacing means comprises:
    a height gauge having an internal thread therein and a scale spaced at a predetermined interval; and
    a height adjusting screw connected to the internal thread for adjusting the vertical displacement of the height gauge.

6. An orthodontic gauge according to claim 1, wherein the handle comprises:
    an upper plate connected to the upper surface of the housing;
    a lower plate connected to the lower surface of the housing; and
    a tapered anchor connected to the bottom surface of the upper plate for adjusting the span between the tweezers.

7. An orthodontic jig according to claim 6, wherein the housing comprises a handle positioning plate comprising positioning recesses spaced at a predetermined angle;
    the lower plate comprises a positioning protuberance fitted into one of the positioning recesses; and
    the handle is rotated around a pivot pin and an angle between the tweezers and the handle is set within 90°.

8. An orthodontic jig according to claim 1, wherein the cusp tip reference means is a plate connected to the displacing means for contacting the cusp surface of a tooth.

9. An orthodontic jig according to claim 1, wherein the cusp tip reference means comprises:
    the cusp tip reference plate connected to the displacing means;
    a frame having a connecting rod and a channel connected with the cusp tip reference plate;
    panels disposed at each side of the frame;
    an occlusal fossae positioning pin connected with the panel for coming in contact with the occlusal fossae of a molar; and
    span adjusting means connected to the panels for adjusting the span between the panels.

10. An orthodontic jig according to claim 9, wherein the cusp tip positioning pin comprises an elongated hole for adjusting the height thereof.

11. An orthodontic jig according to claim 9, wherein the span adjusting means comprises external thread rods; and
    a span adjusting disc disposed between the external thread rods for varying the span of the panels by its rotation.

12. An orthodontic jig according to claim 1, wherein the cusp tip reference means comprises:
    a cusp tip reference plate connected to the displacing means;
    a frame body having a channel connected with the cusp tip reference plate;
    panels disposed at each inner side of the frame body;
    an occlusal fossae positioning pin connected with the panels for coming in contact with the occlusal fossae of a molar; and
    span adjusting means connected through both sides of the frame body and the panels for adjusting the span between the panels.

13. An orthodontic jig according to claim 12, wherein the occlusal fossae positioning pin comprises a plate at an edge thereof.

14. An orthodontic jig according to claim 12, wherein the span adjusting means comprises:
- a span adjusting screw connected through both sides of the frame body and the panels for adjusting the span between the panels; and
- a handle for rotating the span adjusting screw.

15. An orthodontic jig according to claim 14, wherein the span adjusting means further comprises a sliding guide pin parallel to the span adjusting screw for guiding the panels.

16. An orthodontic jig according to claim 1, wherein the cusp tip reference means comprises:
- a cusp tip reference plate connected to the displacing means;
- a reference rod mounted on the cusp tip reference plate;
- a frame body having a cylindrical hole connected with the reference rod by a fastener;
- a reference adjusting rod connected through the upper surface of the frame body; and
- an occlusal fossae positioning plate connected with the frame body for coming in contact with the occlusal fossae of a molar.

17. An orthodontic jig according to claim 1, wherein the orthodontic jig further comprises a lingual bracket positioning device, which includes:
- a vertical frame;
- a lingual bracket support plate inserted into a slot of the lingual bracket;
- first lingual bracket tweezers connected to the vertical frame for gripping the tie wings of the lingual bracket;
- a vertical panel including a hole connected to the cusp tip reference means, a scale disc provided with an elongated hole on a concentric circle and a connecting hole connected to the lingual bracket support plate at the center of the disc; and
- second lingual bracket tweezers connected to the cusp tip reference means for gripping the tie wings of the lingual bracket.

18. An orthodontic jig according to claim 17, wherein the first lingual bracket tweezers comprise:
- a tie wing gripping panel for gripping te tie wings of the lingual bracket;
- a pressing panel for pivoting the tie wing gripping panel;
- a connecting pin connected to the wing gripping panel and the pressing panel, and inserted into the elongated hole; and
- a spring for providing the bracket support plate with restoration force.

19. An orthodontic jig according to claim 1, wherein the orthodontic jig further comprises a lingual bracket positioning device, which includes:
- a wing gripping panel connected with the cusp tip reference means for gripping the tie wing of the lingual bracket;
- a clamp pivotally connected with the wing gripping panel for gripping any part of the lingual bracket.

20. An orthodontic jig for positioning an orthodontic bracket comprising:
- tweezers including two cross over extended parts which are provided with a gripping tip to grip a tie wing of a labial bracket;
- a housing including tweezer support connected with an edge of the tweezers, and a height gauge disposed between the extended parts and connected with a height adjusting screw;
- a bracket support inserted through the housing, wherein one edge thereof is formed with T-shape and the other edge thereof includes a rotation adjusting handle; and
- a cusp tip reference plate fixed with an upper edge of the height gauge for setting the orthodontic position of the bracket from a cusp tip gauge.

* * * * *